US010813959B2

United States Patent
Geletneky et al.

(10) Patent No.: US 10,813,959 B2
(45) Date of Patent: Oct. 27, 2020

(54) CANCER THERAPY WITH A PARVOVIRUS COMBINED WITH BEVACIZUMAB

(71) Applicants: Deutsches Krebsforschungszentrum, Heidelberg (DE); Ruprecht-Karls-Universität Heidelberg, Heidelberg (DE)

(72) Inventors: Karsten Geletneky, Heidelberg (DE); Jean Rommelaere, Heidelberg (DE); Wolfgang Wick, Heidelberg (DE); Antje Wick, Heidelberg (DE); Michael Dahm, Munich (DE)

(73) Assignees: Deutsches Krebsforschungszentrum, Heidelberg (DE); Ruprecht-Karis-Universität Heidelberg, Heidelberg (DE)

( * ) Notice: Subject to any disclaimer, the term of this patent is extended or adjusted under 35 U.S.C. 154(b) by 0 days.

(21) Appl. No.: 15/550,354

(22) PCT Filed: Feb. 10, 2016

(86) PCT No.: PCT/EP2016/025008
§ 371 (c)(1),
(2) Date: Aug. 10, 2017

(87) PCT Pub. No.: WO2016/128146
PCT Pub. Date: Aug. 18, 2016

(65) Prior Publication Data
US 2018/0028583 A1    Feb. 1, 2018

(30) Foreign Application Priority Data
Feb. 11, 2015  (EP) .................................. 15154629

(51) Int. Cl.
| A61K 35/768 | (2015.01) |
| C07K 16/22 | (2006.01) |
| A61K 39/395 | (2006.01) |
| A61K 9/00 | (2006.01) |

(52) U.S. Cl.
CPC .......... *A61K 35/768* (2013.01); *A61K 9/0019* (2013.01); *A61K 39/3955* (2013.01); *C07K 16/22* (2013.01); *A61K 2300/00* (2013.01); *C07K 2317/24* (2013.01); *C07K 2317/76* (2013.01); *C12N 2750/14332* (2013.01)

(58) Field of Classification Search
None
See application file for complete search history.

(56) References Cited

U.S. PATENT DOCUMENTS

2004/0220124 A1   11/2004   Rommelaere et al.

FOREIGN PATENT DOCUMENTS

| WO | 2006075165 A1 | 7/2006 |
| WO | 2010/139400 | 12/2010 |

OTHER PUBLICATIONS

Wojton et al. Impact of tumor microenvironment on oncolytic viral therapy. Cytokine & Growth Factor Reviews 21 (2010) 127-134.*
Friedman et al. Bevacizumab Alone and in Combination With Irinotecan in Recurrent Glioblastoma. J Clin Oncol 27:4733-4740, 2009.*
Geletneky et al. Phase I/IIa study of intratumoral/intracerebral or intravenous/intracerebral administration of Parvovirus H-1 (ParvOryx) in patients with progressive primary or recurrent glioblastoma. BMC Cancer 2012, 12:99.*
Sasaki, Hikaru. "Recent advance and updates in chemotherapy for Glioma." Japanese Journal of Neurosurgery 23.7 (2014): 547-558.
Nagane, M. "Anti-angiogenic therapy for malignant glioma." Gan to kagaku ryoho. Cancer & chemotherapy 41.2 (2014): 141-147.
Ahmadizar et al., Efficacy and Safety Assessment of the Addition of Bevacizumab to Adjuvant Therapy Agents in Cancer Patients: A Systematic Review and Meta-Analysis of Randomized Controlled Trials, Research Articles, PLOS one, published Sep. 2, 2015, 27 pages.

* cited by examiner

*Primary Examiner* — Nianxiang Zou
(74) *Attorney, Agent, or Firm* — FisherBroyles, LLP

(57) ABSTRACT

Described is a pharmaceutical composition comprising (a) a parvovirus and (b) bevacizumab and the use of said composition for treatment of cancer, e.g., a solid tumor.

9 Claims, 4 Drawing Sheets

CANCER THERAPY WITH A PARVOVIRUS COMBINED WITH BEVACIZUMAB

This application is a U.S. National Phase application under 35 USC § 371 of International Application No. PCT/EP2016/025008, filed Feb. 10, 2016, which claims priority from and the benefit of EP Application No. 15154629.8, filed Feb. 11, 2015. Applicant claims the benefits of 35 U.S.C. §§ 119 and 120 to the PCT and GB applications, and the entire disclosures of both applications are incorporated herein by reference in their entireties.

The present invention relates to a pharmaceutical composition comprising (a) parvovirus H-1 in combination with (b) bevacizumab (Avastin®) and the use of said combination for the treatment of cancer, e.g., a solid tumor.

Cancer is the second leading cause of death worldwide. It has been estimated that half of men and one third of women will be diagnosed with some form of cancer during their lifespan. Moreover, because cancer is predominantly a disease of aging, the number of cancer deaths worldwide is predicted to increase about 45% from 2007 to 2030 (from 7.9 million to 11.5 million deaths) due to the increase proportion of elderly people (WHO estimates, 2008). Cancer is also the most costly disease. The latest estimates from the National Cancer Institute showed that the overall economic cost of cancer in the U.S. in 2007 was $226.8 billion and unless more successful preventive interventions, early detection and more efficient treatments will be developed, this already huge economic burden is expected to further grow during the next two decades. Despite significant progresses in the prevention, detection, diagnosis and treatment of many forms of cancer, which is testified by an increase of the percentage of 5-years cancer survivals in U.S. and in Europe over the last thirty years, some tumour types, such as pancreatic, liver, lung, brain remain orphan of effective treatments calling for the development of new therapeutic options. Oncolytic viruses, which exploit cancer-specific vulnerabilities to kill cancer cells while sparing normal cells are fast emerging as promising tools for fighting cancer (Breitbach et al, 2011; Russell et al, 2012). No less than twelve different oncolytic viruses are currently undergoing phase I-III clinical trials against various malignancies (Russell et al, 2012) used alone or in combination with other anticancer agents. Among them, the oncolytic rat parvovirus H-1PV is currently evaluated for safety and first signs of efficacy in a phase I/IIa clinical trial in patients having recurrent glioblastoma multiforme (GBM) (Geletneky et al, 2012).

H-1PV is a small (~25 nm in diameter), non-enveloped icosahedral particle containing a 5.1 kb long single-stranded DNA genome (Cotmore & Tattersall, 2007). The genomic organization of H-1PV consists of two transcriptional units under the control of two promoters, the P4 early promoter and P38 late promoter. P4 regulates the expression of the gene encoding for the non-structural (NS) proteins (NS1 and NS2) and the P38 the one encoding for the capsid (VP) proteins (VP1, VP2, VP3) (Cotmore & Tattersall, 2007). The virus multiplies preferentially in fast dividing cancer cells. This onco-selectivity is not based on a better uptake of the virus by cancerous cells, but rather is due to the fact that cancer cells overexpress factors such as cyclin A, E2F, or CREB/ATF required for virus DNA replication. Furthermore, cancer cells are often defective in their ability to mount an efficient antiviral immune response favouring viral multiplication (Nuesch et al, 2012). The virus is known to activate multiple cell death pathways. Depending on cell type and growing conditions, H-1PV may induce apoptosis (Hristov et al, 2010; Ohshima et al, 1998; Rayet et al, 1998; Ueno et al, 2001), necrosis (Ran et al, 1999), or cathepsin B-dependent cell death (Di Piazza et al, 2007). The virus was able to induce oncolysis even in cancer cells resistant to TRAIL (Tumor Necrosis Factor Related Apoptosis Inducing Ligand), cisplatin and even when Bcl-2 was overexpressed (di Piazza et al., 2007). The latter results suggest that Bcl-2 is not a negative modulator of parvovirus cytotoxicity. Cancer therapy using a parvovirus and its combination with chemotherapy or an HDAC inhibitor has been recently described (WO 2009/083232 A1; WO 2011/113600 A1).

The major non-structural protein NS1 is the master regulator of virus DNA replication, viral gene expression and cytotoxicity. The sole expression of NS1, similarly to the entire virus, is sufficient to induce cell cycle arrest, apoptosis and cell lysis via accumulation of reactive oxygen species and DNA damage (Hristov et al, 2010). As results of its oncolytic activities, the virus has been shown to possess oncosuppressive properties demonstrated in a number of animal models which lay the basis for the launch of the clinical trial against GBM (Geletneky et al, 2012).

Both the growth and metastasis of solid tumors are angiogenesis-dependent (Folkman, J. Cancer Res., 46, 467-73 (1986); Folkman, J. Nat. Cancer Inst., 82, 4-6 (1989); Folkman et al., "Tumor Angiogenesis," Chapter 10, pp. 206-32, in The Molecular Basis of Cancer, Mendelsohn et al., eds. (W.B. Saunders, 1995)). It has been shown, for example, that tumors which enlarge to greater than 2 mm in diameter must obtain their own blood supply and do so by inducing the growth of new capillary blood vessels. After these new blood vessels become embedded in the tumor, they provide nutrients and growth factors essential for tumor growth as well as a means for tumor cells to enter the circulation and metastasize to distant sites, such as liver, lung or bone (Weidner, New Eng. J. Med., 324(1), 1-8 (1991)). When used as drugs in tumor-bearing animals, natural inhibitors of angiogenesis can prevent the growth of small tumors (O'Reilly et al., O'Reilly et al. Cell, 79, 315-28 (1994)). Indeed, in some protocols, the application of such inhibitors leads to tumor regression and dormancy even after cessation of treatment (O'Reilly et al., Cell, 88, 277-85 (1997)). Moreover, supplying inhibitors of angiogenesis to certain tumors can potentiate their response to other therapeutic regimes (e.g., chemotherapy) (see, eg., Teischer et al., Int. J. Cancer, 57, 920-25 (1994)).

One clinically approved candidate as an inhibitor of angiogenesis is Bevacizumab (Avastin®—Genentech/Roche) which is a humanized monoclonal antibody that recognizes and blocks vascular endothelial growth factor (VEGF). VEGF is a chemical signal that stimulates the growth of new blood vessels (angiogenesis). This compound and its preparation are disclosed in U.S. Pat. No. 6,054,297.

WO 2006/075165 A1 relates to a combination therapy which comprises an tumor selective toxic virus and one or more therapeutic agents that reduce tumor blood vessel formation or damage tumor vasculature.

In a recent clinical phase III study ("AVAglio" study, Roche) for treating glioblastoma, bavacizumab was administered together with the chemotherapeutic agent temozolomid and radiation. The results had not been promising as regards the overall survival and experts at the American Society of Clinical Oncology (ASCO) meeting in 2013 came to the conclusion that the expectations for a first-line therapy have not been met.

Therefore, it is the object of the present invention to provide means for an improved cancer therapy.

According to the invention this is achieved by the subject matters defined in the claims.

In the study resulting in the present invention it was asked whether an anti-VEGF antibody, e.g. bevacizumab, synergizes with a parvovirus, e.g. H-1PV or a related rodent parvovirus, in killing cancer cells. It was shown that the administration of bevacizumab potentiates the oncolytic activity of the parvovirus in a synergistic manner in several patients.

Figure 1:
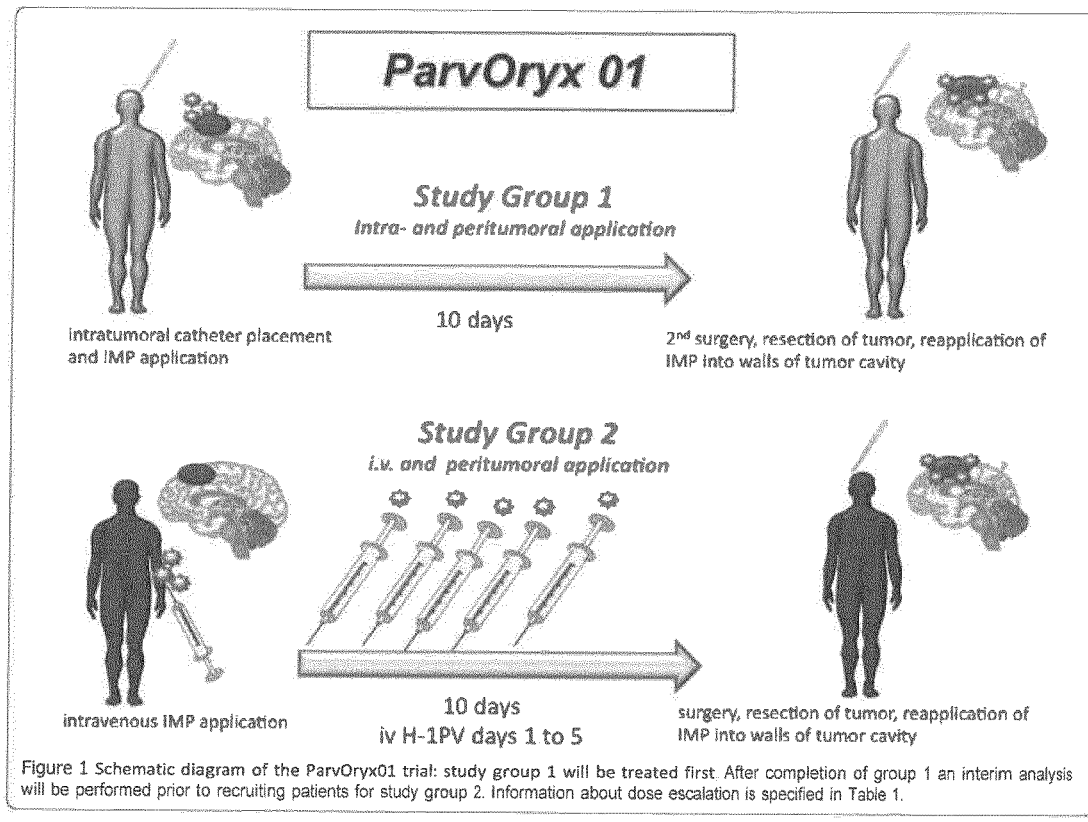
FIG. 1: Trial Design of Clinical Phase I/IIa Study

Preferably, in said pharmaceutical composition the parvovirus H-1 and bevacizumab are present in an effective dose and combined with a pharmaceutically acceptable carrier. "Pharmaceutically acceptable" is meant to encompass any carrier, which does not interfere with the effectiveness of the biological activity of the active ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at an effective dose.

The term "parvovirus" as used herein comprises wild-type or modified replication-competent derivatives thereof, as well as related viruses or vectors based on such viruses or derivatives. Suitable parvoviruses, derivatives, etc. as well as cells which can be used for actively producing said parvoviruses and which are useful for therapy, are readily determinable within the skill of the art based on the disclosure herein, without undue empirical effort.

An "effective dose" refers to amounts of the active ingredients that are sufficient to affect the course and the severity of the disease, leading to the reduction or remission of such pathology. An "effective dose" useful for treating and/or preventing these diseases or disorders may be determined using methods known to one skilled in the art.

Additional pharmaceutically compatible carriers can include gels, bioasorbable matrix materials, implantation elements containing the therapeutic agent, or any other suitable vehicle, delivery or dispensing means or material(s).

Administration of the compounds may be effected by different ways, e.g. by intravenous, intraperetoneal, subcutaneous, intramuscular, topical, intratumoral or intradermal administration. The route of administration, of course, depends on the kind of therapy and the kind of compounds contained in the pharmaceutical composition. The dosage regimen of the parvovirus and bevacizumab is readily determinable within the skill of the art, by the attending physician based an patient data, observations and other clinical factors, including for example the patient's size, body surface area, age, sex, the particular parvovirus, the particular inhibitor etc. to be administered, the time and route of administration, the tumor type and characteristics, general health of the patient, and other drug therapies to which the patient is being subjected. As regards bevacizumab reference is made to the package insert and patient information sheet which are incorporated by reference herewith.

If the parvovirus in the combination with bevacizumab according to the invention comprises infectious virus particles with the ability to penetrate through the blood-brain barrier, treatment can be performed or at least initiated by intravenous injection of the virus. However, a preferred route of administration is intratumoral administration.

Since long-term intravenous treatment is susceptible to becoming inefficient as a result of the formation of neutralizing antibodies to the virus, different modes of administration can be adopted after an initial regimen intravenous viral administration, or such different administration techniques, e.g., intracranial or intratumoral virus administration, can be alternatively used throughout the entire course of parvoviral treatment.

As another specific administration technique, the parvovirus (virus, vector and/or cell agent) can be administered to the patient from a source implanted in the patient. For example, a catheter, e.g., of silicone or other biocompatible material, can be connected to a small subcutaneous reservoir (Rickham reservoir) installed in the patient during tumor removal or by a separate procedure, to permit the parvovirus composition to be injected locally at various times without further surgical intervention. The parvovirus or derived vectors can also be injected into the tumor by stereotactic surgical techniques or by neuronavigation targeting techniques.

Administration of the parvovirus can also be performed by continuous infusion of viral particles or fluids containing viral particles through implanted catheters at low flow rates using suitable pump systems, e.g., peristaltic infusion pumps or convection enhanced delivery (CED) pumps.

A yet another method of administration of the parvovirus composition is from an implanted article constructed and arranged to dispense the parvovirus to the desired cancer tissue. For example, wafers can be employed that have been impregnated with the parvovirus H-1, wherein the wafer is attached to the edges of the resection cavity at the conclusion of surgical tumor removal. Multiple wafers can be employed in such therapeutic intervention. Cells that actively produce the parvovirus H-1, or H-1 based vectors, can be injected into the tumor or into the tumoral cavity after tumor removal.

The therapy with the compound combination is useful for the therapeutic treatment of cancer, in particular (but not exclusively) brain tumor, pancreatic carcinoma, cervical carcinoma, lung cancer, head and neck cancer, breast cancer or colon cancer and can significantly improve the prognosis of said diseases. It can also allow the clinical use of the virus and/or bevacizumab at lower therapeutic doses preserving or even enhancing anticancer efficacy while increasing safety and reducing and/or avoiding side effects. In view of the strong synergistic effect between the parvovirus and bevacizumab it is possible to foresee the reduction of the therapeutic doses, e.g. half or a third of the previously used single component doses are preserving the desired therapeutic effect. In view of the reduced doses (severe) side effects may be reduced or even avoided.

Parvovirus infection effects killing of tumor cells but does not harm normal cells and such infection can, for example, be carried out by intracerebral use of a suitable parvovirus, e.g., parvovirus H-1, or a related virus or vectors based on such viruses, to effect tumor-specific therapy without adverse neurological or other side effects.

The present invention also relates to the use of (a) a parvovirus H-1 and (b) bevacizumab for the preparation of (a) pharmaceutical composition(s) or combination for the treatment of cancer.

The mode of administration of (a) and (b) may be simultaneously or sequentially, wherein, preferably, (a) and (b) are sequentially (or separately) administered. This means that (a) and (b) may be provided in a single unit dosage form for being taken together or as separate entities (e.g. in separate containers) to be administered simultaneously or with a certain time difference. This time difference may be between 1 hour and 1 week, preferably between 12 hours and 3 days. In addition, it is possible to administer the parvovirus via another administration way than bevacizumab. In this regard it may be advantageous to administer either the parvovirus or bevacizumab intratumoraly and the other systemically or orally. In a particular preferred embodiment the parvovirus is administered intratumoraly and bevacizumab intravenously. Preferably, the parvovirus and bevacizumab are administered as separate compounds. Concomitant treatment with the two agents is also possible.

In one preferred embodiment of the present invention, the combination of agents is utilized in the treatment of solid tumours and its metastasis'. Examples are brain tumour, pancreatic carcinoma, cervical carcinoma, lung cancer, head and neck cancer, breast cancer or colon cancer. In a preferred embodiment these tumours are resistant to parvovirus toxicity.

In a further preferred embodiment these tumour to be treated are recurrent tumours. A particular advantage of the pharmaceutical composition of the present invention is that even cancer initiating stem cells can be successfully treated. This has a positive effect as regards the avoidance of the recurrence of the tumours and metastasis formation.

According to the present the parvovirus of the composition is parvovirus H-1 (H-1PV).

Patients treatable by the combination of agents according to the invention include humans as well as non-human animals. Examples of the latter include, without limitation, animals such as cows, sheep, pigs, horses, dogs, and cats.

The present invention further concerns a kit which comprises a first container, a second container and a package insert, wherein the first container comprises at least one dose of a pharmaceutical composition containing parvovirus H-1, the second container comprises at least one dose of a pharmaceutical composition comprising bevacizumab, and the package insert comprises instructions for treating an individual having cancer using the pharmaceutical composition(s).

In the present invention it has been shown for the first time that the combinatorial use of parvovirus H-1PV and bevacizumab may be a valid approach against cancer, in particular gliomas and pancreatic carcinomas.

As regards the treatment of brain tumors, unlike other oncolytic viruses, H-1PV was shown to cross the blood-brain barrier and to infect intracerebral tumors. This offers the chance of boosting the initial local therapy by consecutive intravenous administrations or for interval retreatment without the necessity of craniotomy.

In general, the parvovirus H-1PV is considered to evoke an anticancer vaccination effect based on release of tumor-associated antigens and subsequent immunostimulation. This could lead to long-term effects in prevention of disease relapse, potentially adding to initial oncolysis. This effect is enhanced by using bevacizumab which is an anti-VEGF antibody and acts as an anti-angiogenic agent. In other words, the bevacizumab reduces or normalizes the formation of new blood vessels around the tumor as well as it reduces the immune-inhibitory effects of VEGF. This combination of effects renders the tumor more susceptible to the immune system, in particular after previous therapy with the parvovirus. Patients examples show that this combination therapy leads to either remission or stable disease, even when these patients suffered from progressive recurrent GBM.

The below example explains the invention in more detail.

EXAMPLE 1

Bevacizumab Potentiates the Oncolytic Activity of H-1PV in a Synergistic Manner

A clinical phase I/IIa trial on 18 patients suffering from recurrent malignant gliomas was initiated. This trial aims to investigate the safety, biodistribution, maximum tolerated dose and signs of anti-tumor activity of parvovirus H-1. According to preclinical data the parvovirus will not only include intratumoral virus application but also intravenous treatment.

The application of parvovirus H-1 (GMP-grade preparation) was performed in 2 groups of 12 (group I) and 6 patients (group II). The route of administration differs between group 1 and group 2 (FIG. 1).

Within each group the mode of application is identical, but the dose will be increased if no dose limiting events are observed. In group I the parvovirus H-1 (also called "investigational medicinal product"; IMP) was administered in four dose levels and in group II in 2 dose levels (Table 1).

TABLE 1

Dose schedule for both study groups

| Escalation Level | Study Time | Dose and route of administration | Duration |
|---|---|---|---|
| GROUP I | | | |
| Level 1 Total dose: $1 \times 10^6$ pfu | Day 1 | $5 \times 10^5$ pfu, intratumoral (via catheter) | 15 minutes |
| | Day 10 | $5 \times 10^5$ pfu, intracerebal (direct injection at multiple locations of resection wall) | 15-30 minutes |
| Level 2 Total dose: $5 \times 10^7$ pfu | Day 1 | $2.5 \times 10^7$ pfu, intratumoral (via catheter) | 15 minutes |
| | Day 10 | $2.5 \times 10^7$ pfu, intracerebal (direct injection at multiple locations of resection wall) | 15-30 minutes |
| Level 3 Total dose: $1 \times 10^9$ pfu | Day 1 | $5 \times 10^8$ pfu, intratumoral (via catheter) | 15 minutes |
| | Day 10 | $5 \times 10^8$ pfu, intracerebral (direct injection at multiple locations of resection wall) | 15-30 minutes |
| Level 4 Total dose: $5 \times 10^9$ pfu | Day 1 | $2.5 \times 10^9$ pfu, intratumoral (via catheter) | 15 minutes |
| | Day 10 | $2.5 \times 10^9$ pfu, intracerebral (direct injection at multiple locations of resection wall) | 15-30 minutes |

TABLE 1-continued

Dose schedule for both study groups

| Escalation Level | Study Time | Dose and route of administration | Duration |
|---|---|---|---|
| GROUP II | | | |
| Level 2 Total dose: $5 \times 10^7$ | Day 1-5 | $0.5 \times 10^7$ pfu, intravenous infusion | 2 hours |
| | Day 10 | $2.5 \times 10^7$ pfu, intracerebral (direct injection at multiple locations of resection wall) | 15-30 minutes |
| Level 3 Total dose: $1 \times 10^9$ pfu | Day 1-5 | $1 \times 10^8$ pfu, intravenous infusion | 2 hours |
| | Day 10 | $5 \times 10^8$ pfu, intracerebral (direct injection at multiple locations of resection wall) | 15-30 minutes |

In group 1 the patients received the IMP on day 1 via image guided injection into the tumor tissue. On this day the patient is injected with 50% of the intended overall dose. After an observation period of 9 days the tumor was resected on day 10. After tumor removal the second half of the dose was administered into the walls of the resection cavity by direct injection. With this injection during open surgery the administration of the IMP is completed and no additional virus application was performed.

In group 2 the initial administration of the IMP was via the intravenous route. Subjects received 50% of the intended dose by 5 infusions on days 1 to 5, each infusion containing 10% of the total dose. After the last infusion on day 5 there is an observation period until day 9 and on day 10 tumor resection was performed as in group 1. In analogy to group 1, patients receive the second half of the dose by injection in the tissue surrounding the tumor cavity after tumor removal and no further virus injections were performed in each individual during the course of the trial.

6 patients requested another H-1PV injection on the basis of a compassionate use agreement during resection of tumor recurrence:

Group I Level 1 (intratumoral): 2 patients

Group I Level 2 (intratumoral): 1 patient

Group I Level 3 (intratumoral): 1 patient

Group II Level 3 (intravenous): 2 patients

After tumor resection virus was reapplied in the walls of the tumor cavity, whereas all patients received the same dose of virus of $5 \times 10^8$ PFU.

As a part of the compassionate use program that started in 2013 these patients received after the resection of the tumor recurrence a treatment with bevacizumab.

The below summary (Table 2) of the survival data shows the interesting result that in 5 of 6 patients so far the time between second virus injection and second recurrence or dealth (PFS2) was longer than the time between first virus injection and first recurrence (PFS1). This is untypical for glioblastoma multiforme and a very surprising result.

TABLE 2

(results received as of February 2015)

| DG | ID | Tu ccm | S t/st | OS m | † | PFS1 PV-R1 | PFS2 CU-R2 |
|---|---|---|---|---|---|---|---|
| DG1 | 1-01 | 1.0 | total | 27.4 | † | 12.6 | 14.2 |
| | 1-03 | 3.7 | total | 25.7 | † | 9.0 | 15.7 |
| DG2 | 2-04 | 1.8 | total | 34.9 | | 8.0 | 21.8 |
| DG3 | 3-08 | 13.1 | total | 16.4 | † | 4.3 | 11.6 |

TABLE 2-continued (results received as of February 2015)

| DG | ID | Tu ccm | S t/st | OS m | † | PFS1 PV-R1 | PFS2 CU-R2 |
|---|---|---|---|---|---|---|---|
| DG3 | 5-13 | 15.2 | >90% | 11.3 | | 6.0 | 4.0 |
| | 5-14 | 5.8 | >95% | 11.8 | | 4.0 | 6.6 |

DG: dose group (level),
Tu: tumor size,
S: surgery,
t: total,
st: subtotal,
m: month,
OS: overall survival (month),
PFS: progression free survival (month),
PFS1: start virotherapy, first viral injection - recurrence,
PFS2: start compassionate use, second virus injection - recurrence or death The treatment regimen (all treatments 1.2E9 pfu single dose IMP) in the year 2015 was for Patient 5-13: i.v. treatment on Sep. 2, 2015; peritumoral on Sep. 3, 2015

Patient 5-14: i.v. treatment on Aug. 31, 2015; i.a. treatment on Sep. 1, 2015

1-2 weeks after the virus administration the patients received again Avastin® in a dosage regimen according to the package insert.

Recent Reassessment of the Patients Showed the Following Results:

Patient 1-01: unchanged

Patient 1-03: unchanged

Patient 2-04: OS 40.9 months; patient has died; PFS2 24.2 months

Patient 3-08: unchanged

Patient 5-13: OS 21.3 months; patient has died; PFS2 14 months

Patient 5-14: OS 24.1 months; PFS2 18.4 months; patient is still alive

In the above Table 2 the first four patients (1-01, 1-03, 2-04, 3-08) are from the intratumoral treatment group (Group I) and the last two patients (5-13 and 5-14) are from the intravenous treatment group (Group II).

4 patients responded extremely favorably on the combination of repeated H-1PV injection followed by therapy with bevacicumab. 2 of the 4 patients [2-04 and 5-14] went into remission or stable disease. These data suggest a possible immune stimulation by repeated H-1PV injection, which possibly enhances the effects of bevacicumab.

Figure 2:
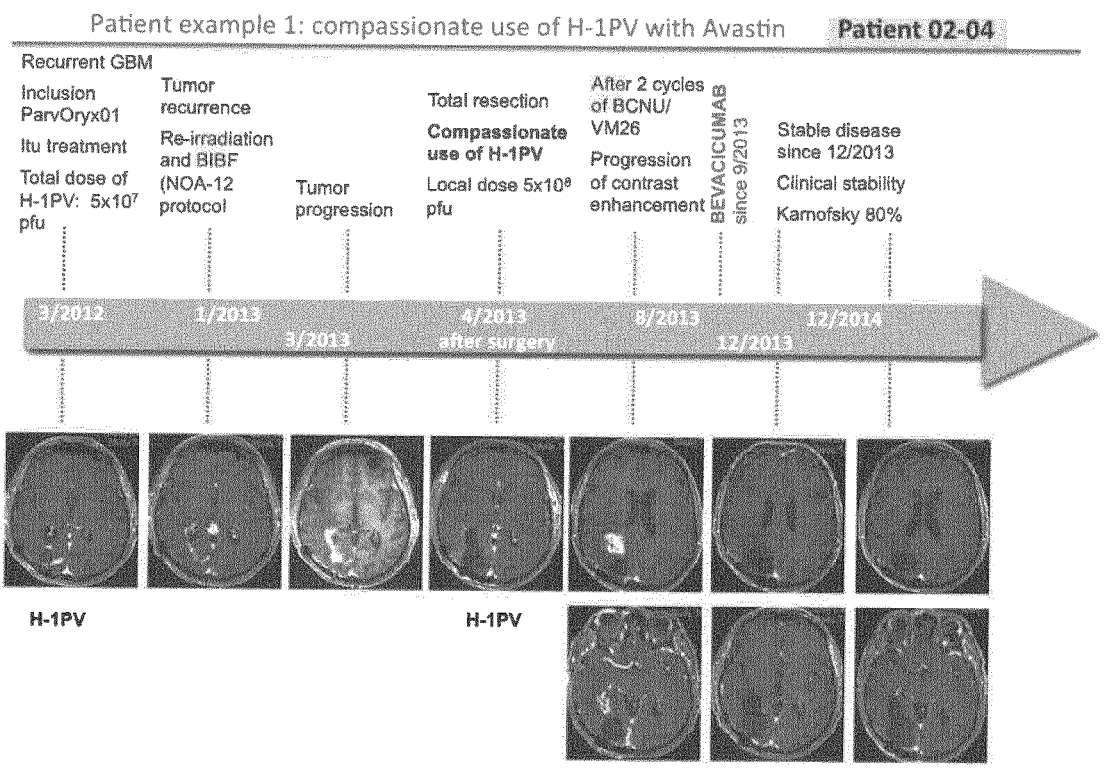
FIG. 2: Compassionate Use of H-1 PV with Avastin® in Patient 2-04
Figure 3:
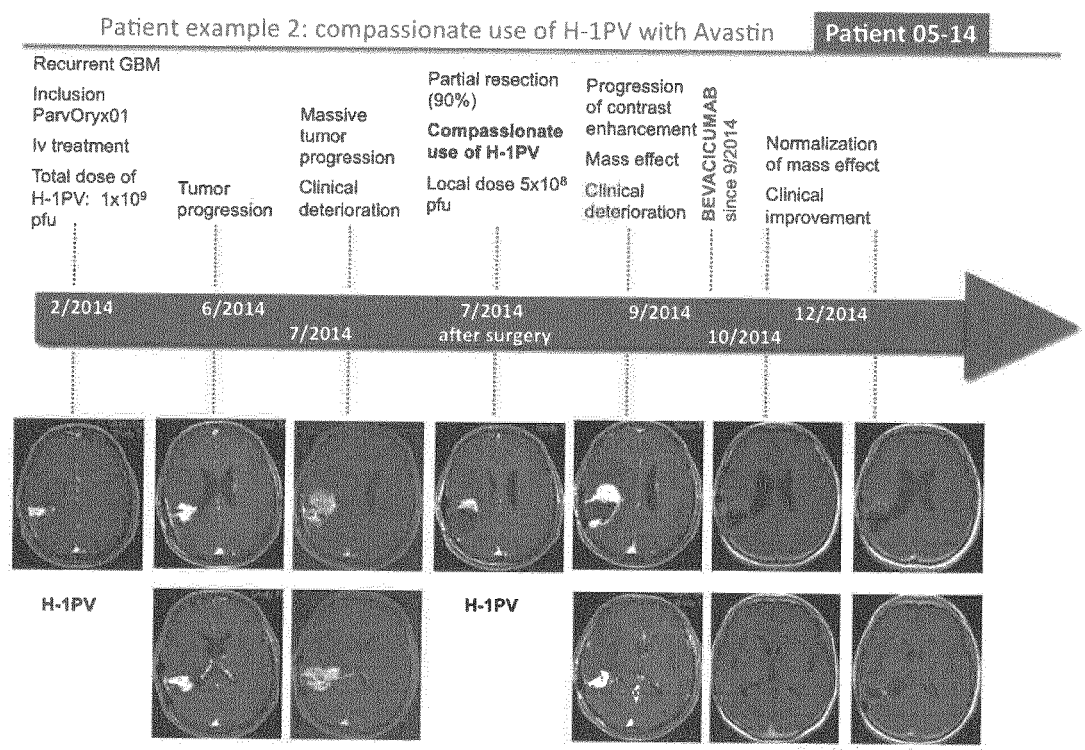
FIG. 3: Compassionate Use of H-1 PV with Avastin® in Patient 5-14

For the two patients 2-04 and 5-13 the treatment protocol and MRI scans are shown in FIGS. 2 and 3.

Figure 4:
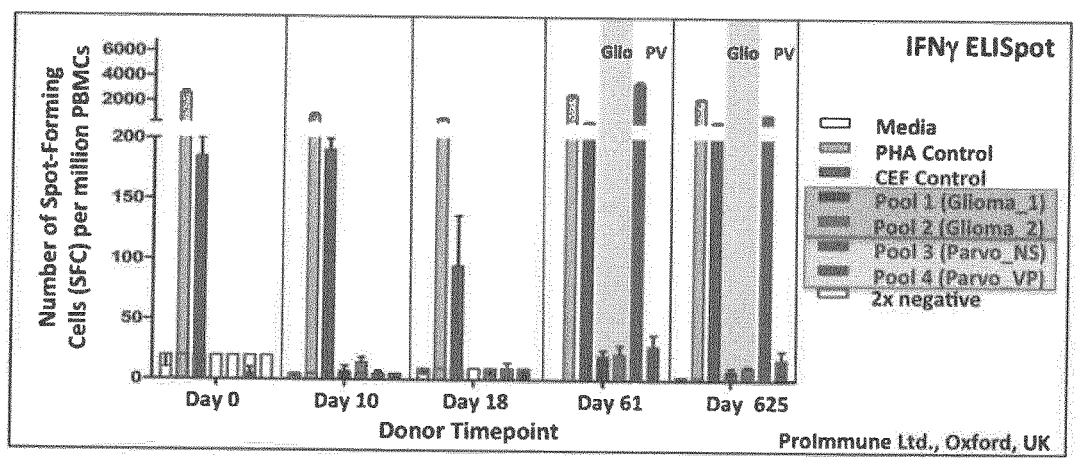
FIG. 4: EliSpot Data of Patient 2-04
Pool 1 & Pool 2: Glioblastoma multiforme (GBM)—specific peptides
Pool 3 & Pool 4: Parvovirus H-1 specific peptides—NS1 and VP The present invention provides a pharmaceutical composition containing (a) parvovirus H-1 in combination with (b) bevacizumab.

The EliSpot Data of patient 2-04 are shown in FIG. 4. It is absolutely surprising that CTL-responses against virus specific NS1 peptides (Poll3; Parvo NS) occur at day 625.

LIST OF REFERENCES

Breitbach C J, Burke J, Jonker D, Stephenson J, Haas A R, Chow L Q, Nieva J, Hwang T H, Moon A, Patt R et al (2011) Intravenous delivery of a multi-mechanistic cancer-targeted oncolytic poxvirus in humans. Nature 477: 99-102

Cotmore S F, Tattersall P (2007) Parvoviral host range and cell entry mechanisms. Adv Virus Res 70: 183-232

Di Piazza M, Mader C, Geletneky K, Herrero y Calle M, Weber E, Schlehofer J, Deleu L, Rommelaere J (2007) Cytosolic Activation of Cathepsins Mediates Parvovirus H-1-Induced Killing of Cisplatin and TRAIL-Resistant Glioma Cells. Journal of Virology 81: 4186-4198

Geletneky K, Huesing J, Rommelaere J, Schlehofer J R, Leuchs B, Dahm M, Krebs O, von Knebel Doeberitz M, Huber B, Hajda J (2012) Phase I/IIa study of intratumoral/intracerebral or intravenous/intracerebral administration of Parvovirus H-1 (ParvOryx) in patients with progressive primary or recurrent glioblastoma multiforme: ParvOryx01 protocol. BMC cancer 12: 99 Hristov G, Kramer M, Li J, El-Andaloussi N, Mora R, Daeffler L, Zentgraf H, Rommelaere J, Marchini A (2010) Through Its Nonstructural Protein NS1, Parvovirus H-1 Induces Apoptosis via Accumulation of Reactive Oxygen Species. J Virol 84: 5909-5922

Nuesch J P, Lacroix J, Marchini A, Rommelaere J (2012) Molecular pathways: rodent parvoviruses-mechanisms of oncolysis and prospects for clinical cancer treatment. Clin Cancer Res 18: 3516-3523

Ohshima T, Iwama M, Ueno Y, Sugiyama F, Nakajima T, Fukamizu A, Yagami K (1998) Induction of apoptosis in vitro and in vivo by H-1 parvovirus infection. The Journal of general virology 79 (Pt 12): 3067-3071

Ran Z, Rayet B, Rommelaere J, Faisst S (1999) Parvovirus H-1-induced cell death: influence of intracellular NAD consumption on the regulation of necrosis and apoptosis. Virus Res 65: 161-174

Rayet B, Lopez-Guerrero J A, Rommelaere J, Dinsart C (1998) Induction of programmed cell death by parvovirus H-1 in U937 cells: connection with the tumor necrosis factor alpha signalling pathway. J Virol 72: 8893-8903

Russell S J, Peng K W, Bell J C (2012) Oncolytic virotherapy. Nat Biotechnol 30: 658-670

Ueno Y, Harada T, Iseki H, Ohshima T, Sugiyama F, Yagami K (2001) Propagation of rat parvovirus in thymic lymphoma cell line C58(NT)d and subsequent appearance of a resistant cell clone after lytic infection. J Virol 75: 3965-3970

The invention claimed is:

1. A method for treating a brain tumor comprising administering a pharmaceutical combination containing (a) a parvovirus in combination with (b) bevacizumab, wherein said parvovirus is H-1 (H-1PV).

2. The method according to claim 1 wherein the pharmaceutical combination containing (a) the parvovirus and (b) bevacizumab is formulated for intratumoral or intravenous administration, and bevacizumab is formulated for intravenous administration.

3. The method according to claim 1 wherein the parvovirus and bevacizumab are sequentially administered.

4. The method according to claim 1 wherein the brain tumor is a solid brain tumor and/or cancer initiating stem cells.

5. The method according to claim 1 wherein the brain tumor is resistant to parvovirus cytotoxicity.

6. The method according to claim 1 wherein the brain tumor is a glioma or recurrent glioblastoma multiforme.

7. The method according to claim 1 wherein the parvovirus and/or bevacizumab are administered by intratumoral or intravenous administration.

8. A kit comprising a first container, a second container and a package insert, wherein the first container comprises at least one dose of a pharmaceutical composition containing parvovirus H-1, the second container comprises at least one dose of a pharmaceutical composition comprising bevacizumab, and the package insert comprises instructions for treating an individual having a brain tumor using the pharmaceutical composition(s).

9. The kit of claim 8, wherein the brain tumor is a glioma or recurrent glioblastoma multiforme.

\* \* \* \* \*